(12) United States Patent
Fogg et al.

(10) Patent No.: US 8,937,212 B2
(45) Date of Patent: Jan. 20, 2015

(54) FEMININE COOLING PAD

(75) Inventors: Michelle Fogg, Salt Lake City, UT (US); John Guynn, Salt Lake City, UT (US)

(73) Assignee: Michelle Fogg, Salt Lake City, UT (US)

( * ) Notice: Subject to any disclaimer, the term of this patent is extended or adjusted under 35 U.S.C. 154(b) by 529 days.

(21) Appl. No.: 13/216,847

(22) Filed: Aug. 24, 2011

(65) Prior Publication Data

US 2012/0053546 A1 Mar. 1, 2012

Related U.S. Application Data

(60) Provisional application No. 61/376,293, filed on Aug. 24, 2010.

(51) Int. Cl.
*A61F 13/15* (2006.01)
*A61F 7/00* (2006.01)
*F25D 3/08* (2006.01)

(52) U.S. Cl.
USPC .............. 604/378; 604/291; 607/112; 62/530

(58) Field of Classification Search
USPC ....................... 604/378, 291; 607/112; 62/530
See application file for complete search history.

(56) References Cited

U.S. PATENT DOCUMENTS

| | | | |
|---|---|---|---|
| 3,871,376 A * | 3/1975 | Kozak | 604/291 |
| 4,259,961 A | 4/1981 | Hood, III | |
| 4,397,315 A | 8/1983 | Patel | |
| 4,930,317 A | 6/1990 | Klein | |
| 5,190,033 A | 3/1993 | Johnson | |
| 5,263,479 A | 11/1993 | Tesch | |
| 5,314,005 A | 5/1994 | Dobry | |
| 5,571,155 A | 11/1996 | Bastille | |
| 5,628,772 A | 5/1997 | Russell | |
| 5,653,741 A | 8/1997 | Grant | |
| 5,674,270 A * | 10/1997 | Viltro et al. | 607/112 |
| 5,800,491 A | 9/1998 | Kolen et al. | |
| 5,989,286 A | 11/1999 | Owens | |
| 6,152,952 A | 11/2000 | Owens | |
| 6,270,873 B1 | 8/2001 | Darnett | |
| 6,942,686 B1 | 9/2005 | Barbut et al. | |

(Continued)

FOREIGN PATENT DOCUMENTS

EP 1688108 8/2006

OTHER PUBLICATIONS

"CVS Peas Cold Pack" http://www.cvs.com/CVSApp/catalog/shop_product_detail.jsp;?filterBy=&skuId=440162&productId=440162—Aug. 25, 2010.

*Primary Examiner* — Jacqueline F. Stephens
(74) *Attorney, Agent, or Firm* — Workman Nydegger

(57) ABSTRACT

A feminine cooling pad is configured for use in cooling a woman's vulva and/or adjacent region. The cooling pad may be configured for single use and be disposable so as to include a liquid permeable layer configured to be oriented toward a user's skin during use. A liquid absorbent layer is adjacent to the liquid permeable layer and configured to absorb bodily fluids or discharges during use. A cooling layer is adjacent to the liquid absorbent layer and configured to provide a cooling effect for a period of time of at least about 15 minutes when the cooling pad is placed against a user's skin. An adhesive layer is adjacent to the cooling layer and adheres the feminine cooling pad to a user's undergarment during use and maintains the cooling pad in a desired orientation relative to the user's body. A feminine heating pad may be provided by including a microwavable material that becomes warm or hot when placed in a microwave oven.

19 Claims, 3 Drawing Sheets

(56) References Cited

U.S. PATENT DOCUMENTS

| | | |
|---|---|---|
| 7,048,976 B2 | 5/2006 | Caceres et al. |
| 7,291,164 B2 | 11/2007 | Peterman et al. |
| 2003/0109910 A1 | 6/2003 | Lachenbruch et al. |
| 2007/0083251 A1 | 4/2007 | von Hoffmann et al. |
| 2007/0142807 A1 | 6/2007 | Lee et al. |
| 2007/0225782 A1 | 9/2007 | Taylor |
| 2009/0312823 A1 | 12/2009 | Patience et al. |
| 2011/0034887 A1* | 2/2011 | Forden et al. ............... 604/291 |

* cited by examiner

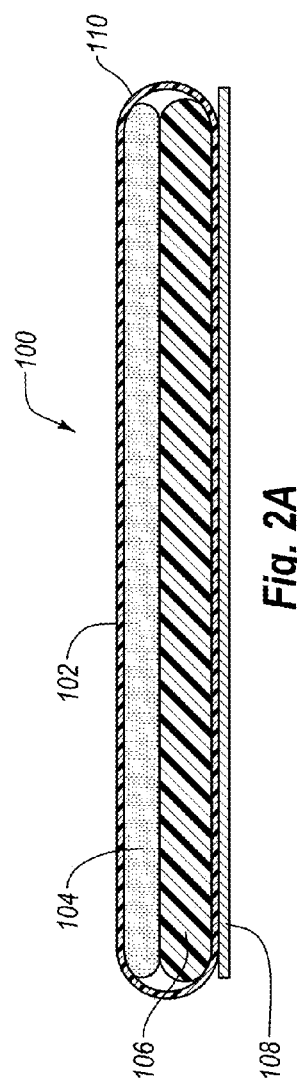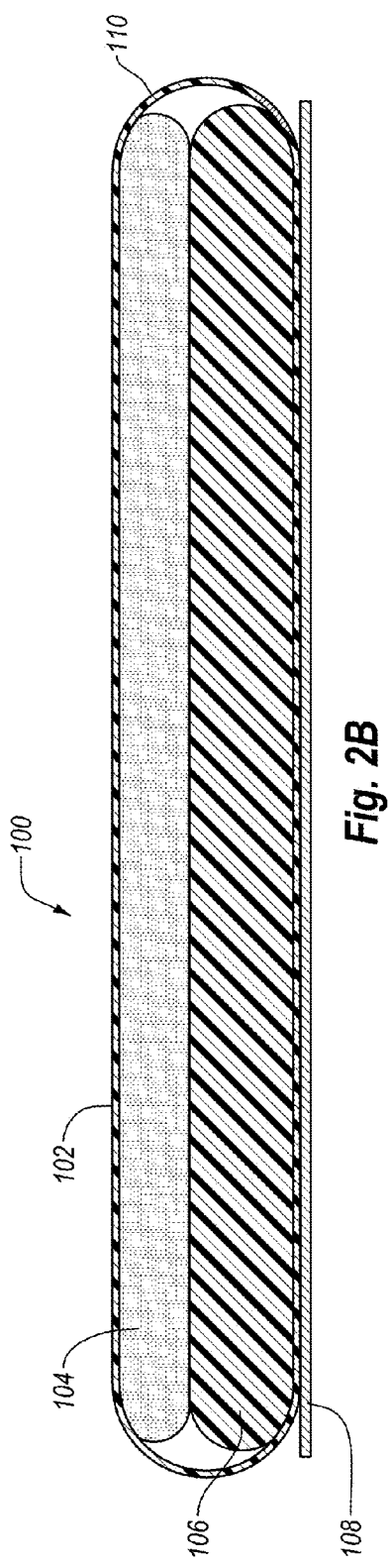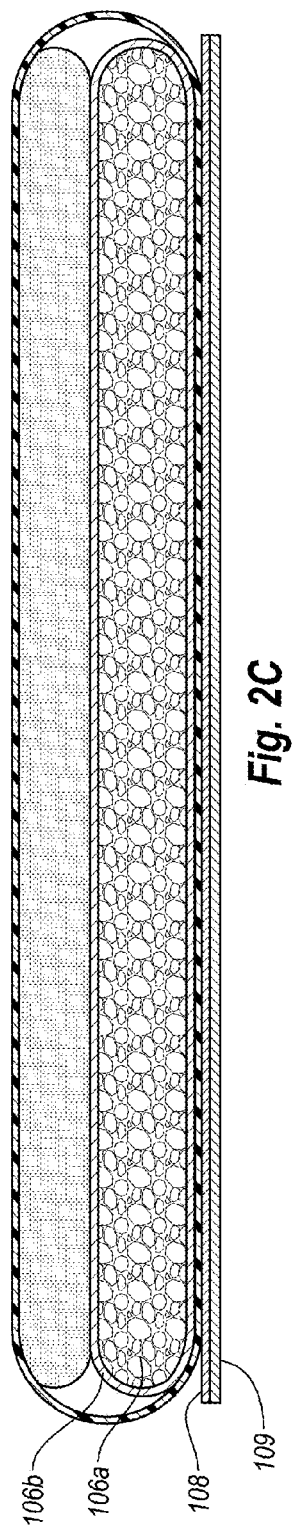

US 8,937,212 B2

FEMININE COOLING PAD

CROSS REFERENCE TO RELATED APPLICATION

This application claims the benefit of U.S. Provisional Application No. 61/376,293, filed Aug. 24, 2010, the disclosure of which is incorporated herein in its entirety.

BACKGROUND OF THE INVENTION

1. Field of the Invention

The invention is in the field of feminine cooling pads.

2. Relevant Technology

A common problem experienced by women is discomfort of the vulva, perineum, and surrounding regions. Such discomfort can have a variety of causes, including but not limited to, vaginal itching and burning as a result of infection (e.g., yeast infection), urethral pain or inflammation as a result of infection (e.g., urinary tract infection), vaginal varicosity (e.g., during pregnancy), damage to the perineum following child birth, and chronic inflammation (e.g., atopic dermatitis).

While various ways of cooling the perineum have been proposed, none have gained acceptance in the market place. Perhaps this is due to inconvenience in the mode of application and/or poor design, causing additional discomfort. If a product is inconvenient and hard to use and/or causes discomfort it will fail in the market place.

U.S. Pat. No. 4,397,315 to Patel and U.S. Patent Publication No. 2007/0142807 to Lee et al. are examples of cooling devices for the perineum that have been proposed. These devices have certain design aspects that limit their usefulness and effectiveness. Accordingly, there remains a need to provide a feminine cooling pad that is designed to more comfortably and conveniently cool and provide relief to the vulva and/or adjacent regions of a woman's body.

SUMMARY

Disclosed are embodiments of feminine cooling pads that provide relief and comfort for women experiencing pain or discomfort of the vulva and/or adjacent regions. According to one embodiment, a self-contained feminine cooling pad that requires no special manipulation or loading of a cooling element prior to use is provided. The feminine cooling pad of this embodiment includes a cooling gel that can be placed in a cooling environment prior to use, such as a refrigerator or freezer, and then removed from the cooling environment and immediately placed over the vulva and/or adjacent region to provide relief and comfort without manipulation or loading of a cooling element.

According to one embodiment, the cooling gel is advantageously smooth, flexible and/or moldable in order to maximize comfort and minimize or eliminate lumps or protruding regions of rigid material. As compared to cooling products that utilize ice chunks, a cooling gel that is smooth, flexible, and/or moldable is far more comfortable to wear and can more evenly distribute the cooling action to the vulva and/or adjacent region. And as compared to chemical cooling media (e.g., that are cooled by a chemical interaction between water and a salt such as a thiosulfate having a positive enthalpy of dissolution), a cooling gel that is cooled in a cooling environment prior to use can provide greater cooling and/or cooling for longer periods of time.

According to another embodiment, a feminine cooling pad is provided that includes an absorbent layer designed to be placed against the vulva, a cooling layer adjacent to the absorbent layer, and an adhesive layer adjacent to the cooling layer designed to adhere the feminine cooling pad to an undergarment of the user. This keeps the feminine cooling pad in the desired position while eliminating the need for cumbersome attachment mechanisms, such as belts or harnesses, thereby enhancing comfort and promoting compliance. The adhesive layer may include a removable backing layer that protects the adhesive prior to use and which can be conveniently removed by the user just prior to use. Eliminating cumbersome belts or harnesses also yields a feminine cooling product that is less visually noticeable when worn beneath ordinary clothing. This can provide enhanced assurance and emotional well being so that the product can be worn in public with minimal embarrassment compared to products that produce unsightly undergarment bulges and lines.

According to one embodiment, the feminine cooling pad is elongated so as to provide cooling to the entire vulva and/or adjacent region. The feminine cooling pad can also have a length so as to extend against the woman's perineum to provide cooling and relieve to the perineum following child birth. The feminine cooling pad may also extend beyond the perineum and over the anal region to provide cooling and relief to that region if desired.

In the case where the feminine cooling pad is sufficiently flexible or moldable when in a cooled condition just prior to use, the feminine cooling pad can be flat. This permits several cooling pads to be stacked in a container that can be placed directly into a refrigerator or freezer after purchase and an individual cooling pad withdrawn from the container as needed just prior to use. This maximizes convenience to the user by providing multiple cooling pads that can be used one after the other as needed and then discarded after use. The feminine cooling pads are advantageously disposable in order to maximize cleanliness to the user and eliminate the need to clean and reuse the product.

In the case where the feminine cooling pad is substantially rigid when in a cooled condition just prior to use, the feminine cooling pad may assume a pre-curved orientation that approximates the curvature of the region of a woman's body to which the product is designed to cover. For example, an elongated product can have an approximate U-shaped configuration in order to conform to the front and back of a woman's crotch region and thereby minimize the amount of flexing that is required to conform the cooling pad to the woman's body prior to use.

The invention can be embodied as a kit of single-use absorbent pads (e.g., 10-25) and one or more reusable cooling gel packs that can be inserted and removed from a compartment within each pad. This permits a cooling gel pack to be removed from a used pad and inserted into a fresh pad (e.g., through a slit down the side of the absorbent pad). Closure means can be used to retain the cooling gel pack within the compartment of the pad during use. In the case where the kit includes multiple single-use absorbent pads and two cooling gel packs, one gel pack can be placed in the freezer while the other one is in use. When the user decides to use a fresh cooling pad, the cooling gel pack is removed from the used pad and placed into the freezer, and the cold gel pack is removed and placed into a fresh pad. This process can be repeated indefinitely for any number of fresh absorbent pads.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings, in which:

FIGS. 2A, 2B, and 2C are side (or cross-sectional) views of embodiments of feminine cooling pads.

DETAILED DESCRIPTION OF THE PREFERRED EMBODIMENTS

Figure 1A:
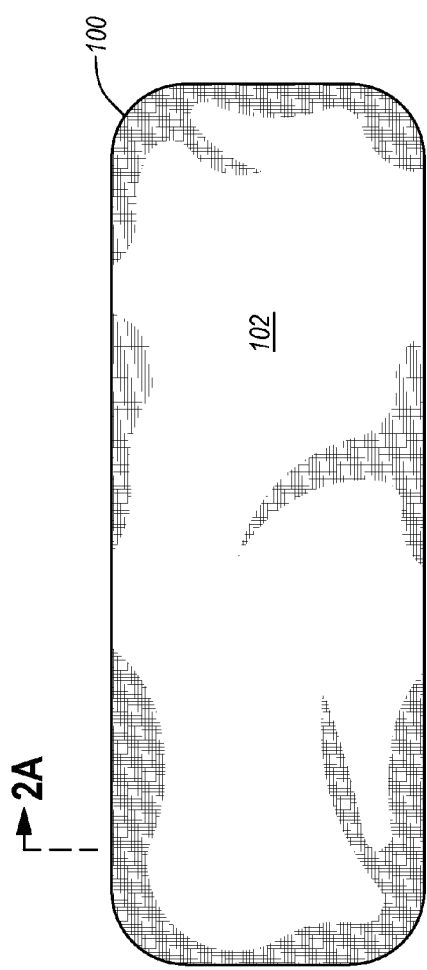
FIGS. 1A and 1B are top (or body facing) views of embodiments of feminine cooling pads.
Figure 1B:
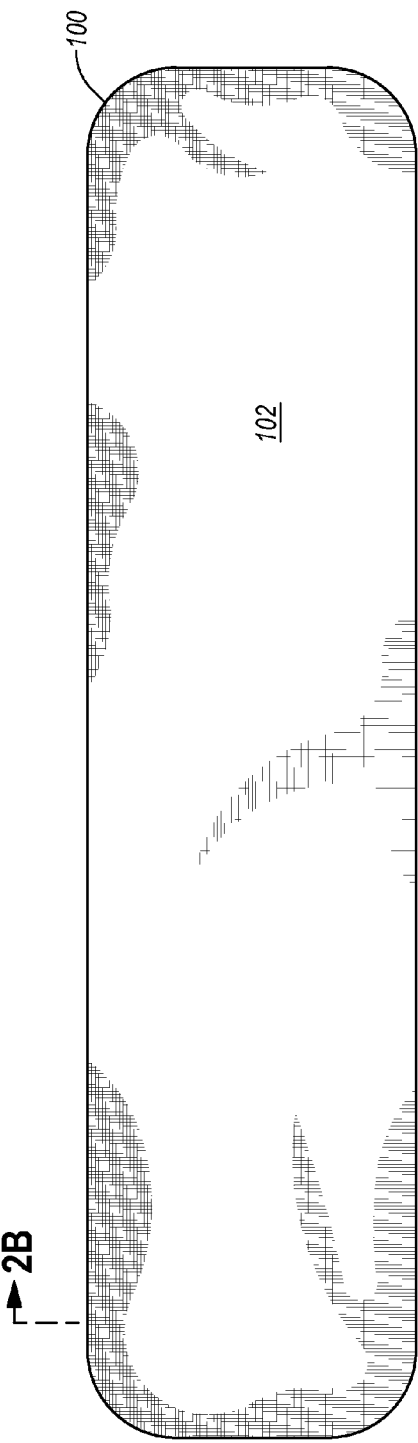
Figure 3A:
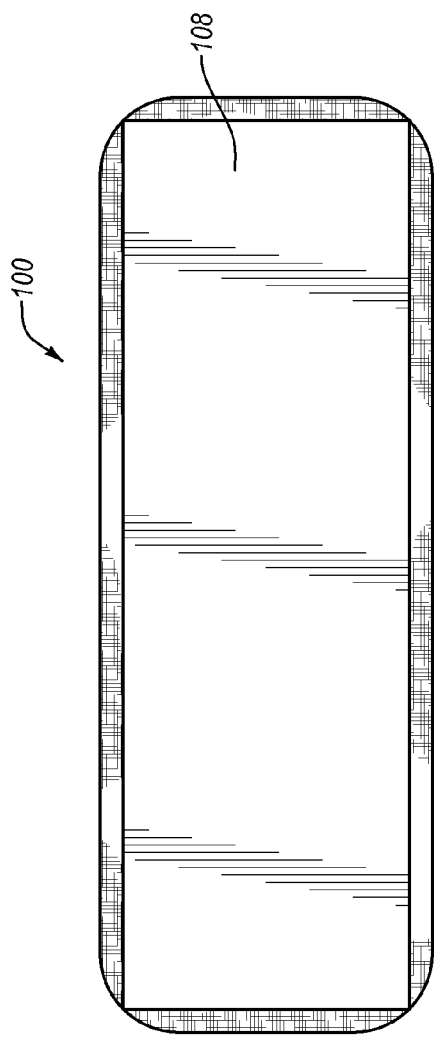
FIGS. 3A and 3B are bottom (or undergarment facing) views of embodiments of feminine cooling pads.
Figure 3B:
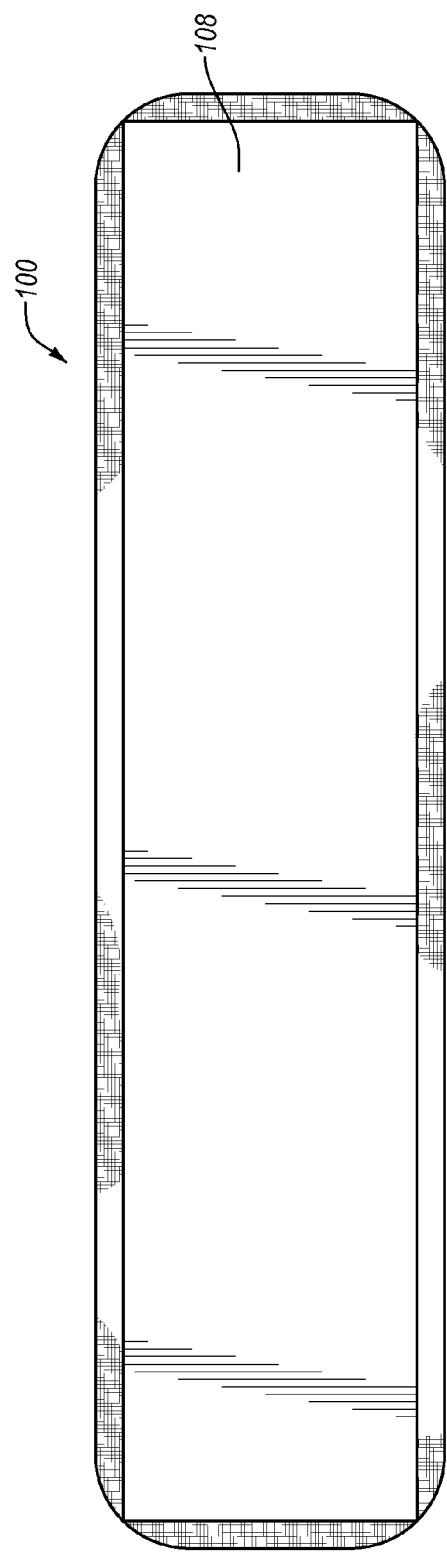

FIGS. 1-3 illustrate embodiments of feminine cooling pads according to the disclosure. The smaller cooling pad shown in FIGS. 1A, 2A and 3A may be characterized as a "light" product, while the larger cooling pad shown in FIGS. 1B, 2B and 3B may be characterized as an "ultra" product. It will be appreciated that the feminine cooling pads can assume a variety of different sizes, thicknesses and/or configurations depending on the particular needs and requirements of the user and/or the intended use of the product.

FIGS. 1A and 1B show top (or body facing) views of differently sized feminine cooling pads 100 showing an enclosure 110, a portion of which forms an outer surface or layer 102 that is designed to be oriented toward the user's body. The outer surface or layer 102 may comprise a layer of a soft woven or cloth material that is soft and comfortable to the touch in order to minimize discomfort when placed against the user's skin. In the case where a liquid absorbent pad or layer is positioned beneath outer surface or layer 102 (see, e.g., FIGS. 2A and 2B), outer surface or layer 102 is advantageously permeable to liquids so as to permit free passage of liquids (e.g., bodily fluids or discharges) through outer surface or layer 102 and into the absorbent pad or layer.

FIGS. 2A and 2B show side (or cross sectional) views of differently sized feminine cooling pads 100. The cooling pads 100 include the outer surface or layer 102 described above, which forms a portion of enclosure 110, an absorbent pad or layer 104 adjacent to or near the outer surface or layer 102, a cooling gel layer 106 adjacent to or near the absorbent pad or layer 104, and an adhesive strip 108 with removable backing layer 109. The absorbent pad or layer 104 and cooling gel layer 106 may be held together by means of the enclosure 110. According to one embodiment, a portion of the enclosure 110 may form a plastic type enclosure to prevent leakage of bodily fluids from the absorbent pad or layer 104 from between the interface of the absorbent pad or layer 104 and the cooling gel layer 106 during use. According to one embodiment, the adhesive strip 108 may be attached to an outer surface of the enclosure 110. Alternatively, the adhesive strip 108 may be attached directly to an exposed surface of a casing surrounding the cooling gel layer 106.

The absorbent pad or layer 104 is positioned beneath the outer surface or layer 102 in order to absorb fluids that may be secreted by the user's body during use. The absorbent pad or layer 104 can also prevent direct contact of the cooling gel layer 106 with the user's skin, thus avoiding injury and providing an initial level of insulation and providing a gradual cooling sensation. The absorbent pad or layer 104 may be constructed from a variety of different materials and may comprise one or more layers of material. According to one embodiment, the absorbent pad or layer 104 is comprised of cotton or other natural fiber having a high degree of liquid absorbance. Alternatively, or in addition, the absorbent pad or layer 104 may include synthetic absorbent materials such as liquid absorbing polymer particles. Particles may be encased within a liquid absorbent and/or liquid permeable casing. As liquids absorbed by the absorbent pad or layer 104 tend to be more conductive of heat and cold than the absorbent pad or layer 104, the absorption of bodily fluid may increase the flow of heat through the absorbent pad or layer 104 and thereby enhance the cooling effect of the cooling gel layer 106.

The cooling gel layer 106 may include any cooling gel capable of being placed in a cooling environment and then provide a cooling effect over an extended period of time (e.g., at least about 15 minutes, or at least about 30 minutes, or at least about 45 minutes, or at least about 1 hour). An appropriate cooling gel may be enclosed within a liquid impermeable casing, such as a plastic pouch.

An example of a cooling gel is a composition that includes water, salt, and a gelling agent, such as cellosize (hydroxyethyl cellulose). The gel may also include colorants (e.g., green or blue) and preservatives. An anti-freeze material, such as ethylene glycol, propylene glycol, or isopropyl alcohol, may be added in order to soften the cooled gel and render it more flexible or moldable after being cooled in a freezer. The amount of anti-freeze material can be varied to provide a desired level of flexibility and/or moldability of the product when cooled to freezing (e.g., below 32° F. or 0° C.). Some amount of congealing of the water may be desirable as allowing water to undergo a phase change may increase the overall ability of the cooling gel to provide a desired cooling effect.

In some embodiments, as illustrated in FIG. 2C, it may be desirable to include freezable cooling particles or beads 106a within a flexible casing 106b. Freezable cooling particles or beads 106a may be comprised of hollow plastic or glass spheres that contain water or salt water without an anti-freeze material (or a relatively small amount of anti-freeze material). This permits the water in the particles or pellets to freeze and/or be cooled to below 0° C. without self-adhering. This, in turn, permits the overall cooling pack to remain flexible and conformable to the user's body after being cooled in a freezer.

The cooling layer 106 may alternatively include a two part chemical cooling media that can supplement and/or replace cooling by a freezable cooling gel. Two part chemical cooling media known in the art can be used.

The adhesive layer 108 may comprise a variety of different adhesive materials known in the art. According to one embodiment, the adhesive material is able to maintain adequate adhesion to a user's undergarment even at cool or cold temperatures. Cool temperatures within a refrigerator are typically between 33-45° F. (0.5-10° C.). Cold temperatures within a freezer are typically between 0-32° F. (−20-0° C.). To protect the adhesive and/or prevent self-adhesion of adjacent cooling pads, the adhesive layer 108 may include a removable backing layer, such as a strip of polymer coated paper or a polymer sheet. The removable backing layer may include a laterally extending tab (not shown) that assists the user in removing the backing layer prior to use.

FIGS. 3A and 3B show bottom (or undergarment facing) views of differently sized feminine cooling pads 100 showing the adhesive strip 108 that is designed to be oriented toward the user's undergarment. The adhesive strip 108 advantageously covers a majority of the undergarment facing surface of the cooling pad in order to maximize the area of interface between the adhesive strip 108 and the undergarment. This enhances the ability of the adhesive strip 108 to adhere and maintain the cooling pad 100 in a desired orientation relative to the user's undergarment and body during use. According to one embodiment, a portion of absorbent pad 104 and/or enclosure 110 may extend beyond the adhesive strip 108 in order to capture additional body fluids that may be excreted by the user's body.

According to one embodiment, the corners of the cooling pad may be rounded in order to prevent the corners of a relatively rigid cooling pad from poking or otherwise irritating the user's body during placement and use. Rounding the corners of the feminine cooling pad may be particularly useful in the case where the cooling layer becomes rigid when frozen.

The cooling pad may assume other configurations in order to maximize comfort to the user. As discussed above, in the case where the feminine cooling pad is desired to wrap around a user's crotch, it may be desirable for the cooling pad to have a curved (e.g., U-shaped) configuration prior to use. This reduces or eliminates the amount of bending that must be performed during placement of the relatively rigid device over a woman's body. This, in turn, maximizes comfort of the product and compliance by the user.

The feminine cooling pads can have a variety of different sizes and/or thicknesses to provide a desired level of comfort, cooling ability and/or coverage. According to one embodiment, a "light" cooling pad may have a length of about 6 inches and a width of about 2 inches. According to another embodiment, an "ultra" cooling pad may have a length of about 9 inches and a width of about 3 inches.

Nevertheless, it will be appreciated that the cross sectional area and dimensions can be selected depending on the intended use. According to one embodiment, the length can be in a range of about 4 inches to about 12 inches, or about 5 inches to about 10 inches, or about 6 inches to about 9 inches. According to another embodiment, the width can be in a range of about 1 inch to about 4 inches, or about 1.5 inch to about 3.5 inches, or about 2 inches to about 3 inches.

According to one embodiment, the cross sectional thickness of the absorbent layer in a "light" cooling pad may be about ⅛ inch and the cross sectional thickness of the cooling gel layer may be about ¼ inch. According to another embodiment, the cross sectional thickness of the absorbent layer in an "ultra" cooling pad may be about ¼ inch and the cross sectional thickness of the cooling gel layer may be about ½ inch.

Nevertheless, it will be appreciated that the cross sectional thicknesses of the absorbent layer and cooling gel layer can be selected depending on the intended use. According to one embodiment, the cross sectional thickness of the absorbent layer can be in a range of about 1/16 inch to about ½ inch, or about 3/32 inch to about ⅜ inch, or about ⅛ inch to about ¼ inch. According to another embodiment, the cross sectional thickness of the cooling gel layer can be in a range of about ⅛ inch to about ¾ inch, or about 3/16 inch to about ⅝ inch, or about ¼ inch to about ½ inch.

In addition to the foregoing, it is possible to provide a microwaveable material as a separate layer or as part of the cooling layer. The microwaveable material permits the cooling pad to also function as a heating pad when it is desired to provide heat instead of and/or prior to and/or subsequent to cooling. According to one embodiment, the microwaveable material includes an organic product such as rice or other grain that can become hot when placed into a microwave. It is generally desirable to cool the perineum for the first 24-48 hours post partum, and apply heat 48 hours post partum.

Alternatively, the heating pad may include a two part chemical heating media that can supplement and/or replace heating by a microwaveable material. Two part chemical heating media known in the art can be used.

The feminine cooling pads disclosed herein can be used to alleviate pain and discomfort caused by a wide variety of feminine ailments, such as pain and discomfort of the vulva, perineum, and surrounding regions. Such discomfort can have a variety of causes, including but not limited to, vaginal itching and burning as a result of infection (e.g., yeast infection), urethral pain or inflammation as a result of infection (e.g., urinary tract infection), vaginal varicosity, which may involve formation of varicose veins in the vulva or vagina during pregnancy due to increased pressure by the fetus that prevents adequate blood drainage, damage to the perineum following child birth, or chronic inflammation (e.g., atopic dermatitis).

The invention can be embodied as a kit of single-use absorbent pads (e.g., 10-25) and one or more reusable cooling gel packs that can be inserted and removed from a compartment within each pad. This permits a cooling gel pack to be removed from a used pad and inserted into a fresh pad (e.g., through a slit down the side of the absorbent pad). Closure means can be used to retain the cooling gel pack within the compartment of the pad during use. In the case where the kit includes multiple single-use absorbent pads and two cooling gel packs, one gel pack can be placed in the freezer while the other one is in use. When the user decides to use a fresh cooling pad, the cooling gel pack is removed from the used pad and placed into the freezer, and the cold gel pack is removed and placed into a fresh pad. This process can be repeated indefinitely for any number of fresh absorbent pads. A similar process of use and replacement can be used to serially refresh warming pads as disclosed herein.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A feminine cooling pad that remains flexible when cooled in a freezer comprising:
    a liquid absorbent material forming a liquid absorbent layer having an exterior surface configured to be oriented toward a user's skin and absorb bodily fluids or discharges during use and an interior surface;
    a gel pack comprised of a gel material enclosed within a liquid impermeable polymer casing and forming a separate cooling layer adjacent to the interior surface of the liquid absorbent layer, wherein the gel pack can be repeatedly placed in a cooling environment prior to use and will subsequently provide a cooling effect for a period of time of at least about 15 minutes when the cooling pad is placed against a user's skin, wherein the cooling layer remains flexible when cooled to a temperature below 0° C. in order for the cooling layer to be conformable to a user's body; and
    an adhesive strip adjacent to a side of the cooling layer opposite to a side that is adjacent to the liquid absorbent layer, wherein the adhesive strip further includes a removable backing layer.

2. A feminine cooling pad as in claim 1, wherein the liquid absorbent layer comprises a cotton absorbent pad.

3. A feminine cooling pad as in claim 1, wherein the liquid absorbent layer has a cross sectional thickness extending between the exterior surface and the interior surface in a range of about 1/16 inch to about ½ inch and wherein the cooling layer has a cross sectional thickness in a range of about ⅛ inch to about ¾ inch that is in addition to the cross sectional thickness of the liquid absorbent layer.

4. A feminine cooling pad as in claim 1, wherein the liquid impermeable polymer casing is interposed between the gel material and the liquid absorbent material.

5. A feminine cooling pad as in claim 4, wherein the gel material is formulated so as to remain flexible or moldable at a temperature in a range of about 0° F. to about 32° F.

6. A feminine cooling pad as in claim 1, wherein the gel pack comprises a plurality of particles or beads, each comprised of a portion of the gel material enclosed within a portion of the liquid impermeable polymer casing, that become individually rigid but do not self adhere when frozen.

7. A feminine cooling pad as in claim 1, further comprising a liquid permeable layer adjacent the exterior surface of the liquid absorbent layer.

8. A feminine cooling pad as in claim 7, wherein the liquid permeable layer comprises a cotton woven material.

9. A feminine cooling pad as in claim 1, wherein the adhesive strip includes a layer of adhesive material that remains adhesive when cooled to a temperature between about 33° F. to about 45° F.

10. A feminine cooling pad as in claim 1, wherein the feminine cooling pad has a length in a range of about 4 inches to about 12 inches and a width in a range of about 1 inch to about 4 inches.

11. A kit for use in serially refreshing a cooling pad comprising a plurality of liquid absorbent layers and the gel pack as in claim 1, and wherein each liquid absorbent layer includes an interior compartment for holding the gel pack therein, and wherein the gel pack is selectively insertable and removable from the interior compartment of each liquid absorbent layer so that the gel pack can be removed from an interior compartment of a used liquid absorbent layer and reused by being inserted within an interior compartment of a fresh liquid absorbent layer.

12. A method of cooling a vulva or adjacent tissue of a woman comprising,
obtaining a feminine cooling pad as in claim 1;
causing the cooling layer to become cool or frozen; and
placing the cooling pad adjacent to a region of a user's body.

13. A method of warming a vulva or adjacent tissue of a woman comprising,
obtaining a feminine cooling pad as in claim 1;
causing the feminine cooling pad to become warm or hot; and
placing the feminine cooling pad adjacent to a region of a user's body.

14. A feminine cooling pad comprising:
a liquid absorbent layer configured to be oriented toward a user's skin and absorb bodily fluids or discharges during use;
a cooling layer adjacent to the liquid absorbent layer that can be repeatedly placed in a cooling environment prior to use and which will subsequently provide a cooling effect for a period of time of at least about 15 minutes when the cooling pad is placed against a user's skin;
an adhesive strip adjacent to a side of the cooling layer opposite to a side that is adjacent to the liquid absorbent layer; and
a removable backing layer for protecting the strip of adhesive material prior to use.

15. A feminine cooling pad as in claim 14, wherein the adhesive strip remains adhesive when cooled to a temperature between about 33° F. to about 45°.

16. A feminine cooling pad as in claim 14, wherein the cooling layer includes a gel pack comprised of a gel material enclosed within a liquid impermeable casing and that can be repeatedly placed in a cooling environment prior to use and that remains flexible and conformable to a user's body when cooled to a temperature below 0° C.

17. A feminine cooling pad as in claim 14, wherein the cooling layer includes a two part chemical cooling composition enclosed within a liquid impermeable casing that provides cooling upon mixing two components together.

18. A feminine cooling pad as in claim 14, the feminine cooling pad comprising a microwaveable material that becomes hot when placed into a microwave oven and which permits the feminine cooling pad to alternatively provide heating instead of cooling.

19. A feminine cooling pad comprising:
a liquid absorbent pad having a liquid absorbent layer configured to be oriented toward a user's skin and absorb bodily fluids or discharges during use;
a cooling gel pack comprised of a plurality of particles or beads, each comprised of a gel material enclosed within a liquid impermeable polymer casing, wherein the cooling gel pack can be repeatedly placed in a cooling environment prior to use and subsequently provide a cooling effect for a period of time of at least about 15 minutes when placed against a user's skin;
an adhesive strip adjacent to a side of the cooling gel pack opposite to a side fo the gel pack that is adjacent to the liquid absorbent layer; and
a removable backing layer on the strip of adhesive material.

* * * * *